US008392355B2

(12) United States Patent
Kennedy et al.

(10) Patent No.: US 8,392,355 B2
(45) Date of Patent: Mar. 5, 2013

(54) COMPUTER SOFTWARE FOR VISUALIZING GENOTYPING DATA

(75) Inventors: Giulia C Kennedy, San Francisco, CA (US); Yaron Turpaz, San Jose, CA (US); Chun Zhang, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 52 days.

(21) Appl. No.: 12/879,419

(22) Filed: Sep. 10, 2010

(65) Prior Publication Data

US 2011/0060768 A1    Mar. 10, 2011

Related U.S. Application Data

(63) Continuation of application No. 11/674,726, filed on Feb. 14, 2007, now Pat. No. 7,818,281.

(60) Provisional application No. 60/773,282, filed on Feb. 14, 2006.

(51) Int. Cl.
*G06F 7/00* (2006.01)
*G06F 3/14* (2006.01)
*G06F 3/00* (2006.01)
*G01N 33/50* (2006.01)

(52) U.S. Cl. .......................................... 706/62; 702/20

(58) Field of Classification Search .................. 706/62
See application file for complete search history.

(56) References Cited

U.S. PATENT DOCUMENTS

2004/0241730 A1*  12/2004  Yakhini et al. .................... 435/6

OTHER PUBLICATIONS

Sabatti et al. (Sabatti), Bayesian Gaussian Mixture Models for High Density Genotyping Arrays [online], Apr. 2005 [retrieved on Jul. 16, 2011]. Retrieved from the Internet:<URL:http://preprints.stat.ucla.edu/421/March28Affy2.pdf>.*
Sobel, E. and Lange, K. Descent graphs in pedigree analysis: Applications to haplotyping, location scores, and marker-sharing statistics. Am J Hum Genet, 58, 1323-1337 [online] 1996 [retrieved on Oct. 19, 2011]. Retrieved from the Internet:< URL: http://www.ncbi.nlm.nih.gov/pmc/articles/PMC1915074/pdf/ajhg00019-0229.pdf>.*
Daly et al. (Daly), "High-resolution haplotype structure in the human genome", 2001.*
Daly et al., High-resolution haplotype structure in the human genome, 2001.
Nyholt, Genehunter: Your One-Stop shop for statistical Genetic Analysis?; 2002.

* cited by examiner

*Primary Examiner* — Jeffrey A Gaffin
*Assistant Examiner* — Nathan Brown, Jr.
(74) *Attorney, Agent, or Firm* — Affymetrix, Inc.

(57) ABSTRACT

A computer system for visualizing recombination events in a group of individuals is provided. According to one aspect of the invention, high-density SNP genotype data is obtained from related individuals in a family. A pedigree is created, haplotypes are reconstructed and likely recombination breakpoints are identified with the use of publicly available computer programs. A software tool is then used facilitate the visualization of the recombination events in the family.

51 Claims, 5 Drawing Sheets

COMPUTER SOFTWARE FOR VISUALIZING GENOTYPING DATA

RELATED APPLICATIONS

This application is a continuation of U.S. patent application Ser. No. 11/674,726, filed on Feb. 14, 2007, now U.S. Pat. No. 7,818,281, which claims the benefit of U.S. Provisional Patent Application No. 60/773,282, filed on Feb. 14, 2006. Each of these applications is incorporated herein in its entirety by reference for all purposes.

BACKGROUND OF THE INVENTION

The present invention relates to the field of computer systems. More specifically, the present invention relates to computer systems for visualizing biological information. Devices and computer systems for forming and using arrays of materials on a substrate are known. New genotyping technologies, such as the Affymetrix SNP 100K and 500K assays (commercially available from Affymetrix, Inc., Santa Clara, Calif. 94024, USA), have paved the way for large scale genotyping analysis.

SUMMARY OF THE INVENTION

An improved computer-aided system for visualizing and determining information is disclosed. In one aspect of the invention, a software tool (methods and computer software products) for visualizing recombination events in families is provided. In a preferred embodiment, high-density SNP genotype data (e.g., 100 k, 500 k, MIP (targeted genotyping) assays from Affymetrix, Illumina genotyping assays and any other suitable genotyping methods including resequencing, de novo sequencing) is obtained from related individuals in a family. A pedigree is constructed based on the known relationships of the individuals. A computer software module, such as the publicly available Merlin, uses the genotype and pedigree information to reconstruct haplotypes and identify likely recombination breakpoints. A software tool is then used to facilitate visualization. The visualization software can be illustrated using an exemplary embodiment, "Chromosome Painter" that takes this information on recombination breakpoints and grandparental assignment and color-codes the data for each chromosome so that it can be visualized in color.

DETAILED DESCRIPTION OF THE INVENTION

A. General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed W. H. Freeman Pub., New York, N.Y. all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (international Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598(U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et. al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et. al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861, 245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred. to in: Maniatis et al. *Molecular Cloning: A Laboratory Manual* ($2^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments, See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 5,025,601, 6,090,555, 6,141,096, 6,185,030, 6,201,639, 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, inc., $2^{nd}$ ed. 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), Ser. Nos. 10/065,856, 10/065,868, 10/328,818, 10/328,872, 10/423,403, and 60/482,389.

B. Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a biopolymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "effective amount" as used herein refers to an amount sufficient to induce a desired result.

The term "fragmentation" refers to the breaking of nucleic acid molecules into smaller nucleic acid fragments. In certain embodiments, the size of the fragments generated during fragmentation can be controlled such that the size of fragments is distributed about a certain predetermined nucleic acid length.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., *Science* 254, 1497-1500 (1990), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage disequilibrium" or sometimes refer by allelic association as used herein refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, (or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces in many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

C. Embodiments

Synthesized nucleic acid probe arrays, such as Affymetrix GeneChip® probe arrays, and spotted arrays, have been used to generate unprecedented amounts of information about biological systems. For example, the GeneChip® Human Genome U133 Pus 2.0 Array available from Affymetrix. Inc. of Santa Clara, Calif., is comprised of one microarray containing 1,300,000 oligonucleotide features covering more than 47,000 transcripts and variants that include 38,500 well characterized human genes. Other examples of GeneChip® arrays are targeted to provide data aimed at different areas of specialization. Examples of specialized uses include analysis of Single Nucleotide Polymorphisms (SNPs) provided by the GeneChip® Human Mapping 10K, 100K, or 500K Arrays, or analysis of alternative splicing events provided by the GeneChip® Human Exon 1.0 ST Array or analysis of detecting germ line and deterplasmic mutations provided by the GeneChip® Human Mitochondrial REsequencing Array 2.0. Analysis of data from such microarrays may lead to the development of new drugs and new diagnostic tools.

Figure 1:
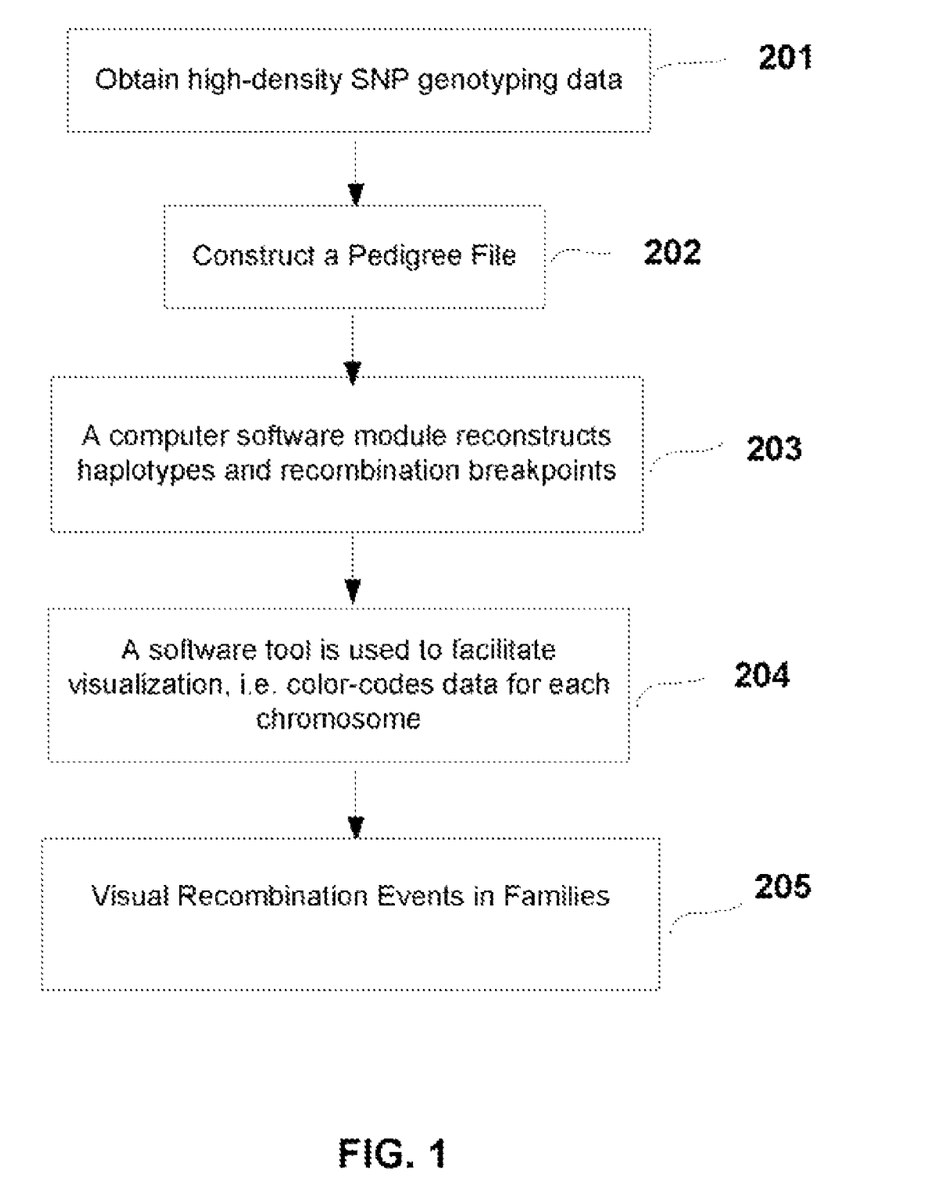
FIG. 1 illustrates the high level flow of the method used to visualize recombination events in families according to an embodiment of the present invention.
Figure 3:
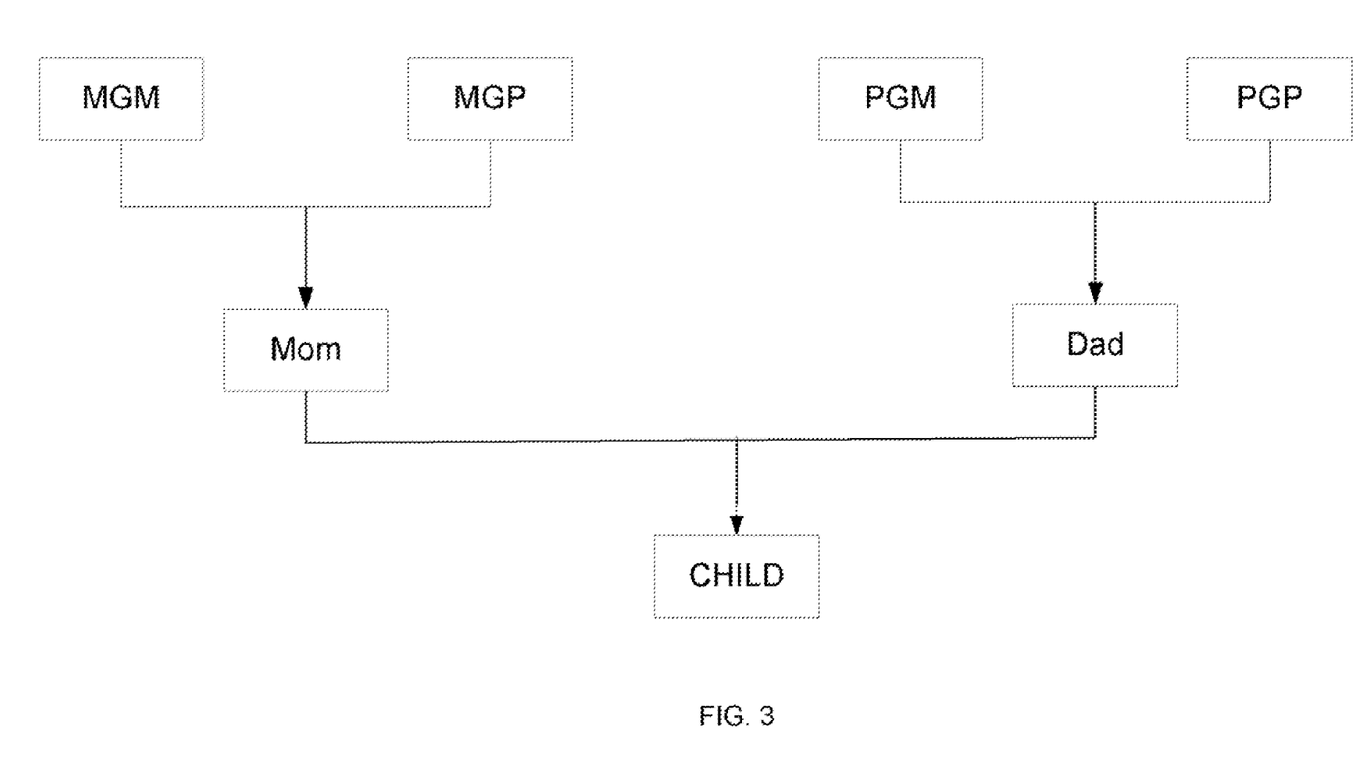
FIG. 3 illustrates an example of a pedigree file.

In one aspect of the invention, a software tool (methods and computer software products) for visualizing recombination events in families is provided. FIG. 1 illustrates a high level flow of an example of the method used to visualize recombination events in families. This diagram is merely an example, which should not unduly limit the scope of the claims. One of ordinary skill in the art would recognize many variations, alternatives, and modifications. At step 201, in a preferred embodiment, high-density SNP genotyping data (e.g., 100 k, 500 k, MIP (targeted genotyping) assays from Affymetrix, Illumina genotyping assays and any other suitable genotyping methods including resequencing, de novo sequencing) is obtained from related individuals in a family. At step 202, a pedigree is constructed based on the known relationships of the individuals. A pedigree file can contain information about family relationships and other characteristics, for example, gender and genetic data (disease and marker phenotypes). The pedigree file can be used to describe individuals which include people, animals, plants, insects, etc. In the preferred embodiment, pedigree files are created from a group of individuals where high-density SNP genotyping data can be obtained. There are several software tools that are available to create pedigree files, for example, Pedigree Drawing Tool from Progeny, PED 5 Pedigree Drawing Software from Medgen, CircuSoft OPEDiT pedigree drawing software from CircuSoft Instrumentation, etc. FIG. 3 illustrates an example of a pedigree file according to an embodiment of the present invention. This diagram is merely an example, which should not unduly limit the scope of the claims. One of ordinary skill in the art would recognize many variations, alternatives, and modifications. In this example, there are two sets of grandparents: Paternal (PGM (paternal grandmother) and PGP (paternal grandpa)) and MGM (maternal grandmother) and MGP (maternal grandpa), father, mother and a child. Other examples may include great grandparents, aunts, uncles, cousins, step parent, step child, cousins, etc.

At step 203, a computer software module, such as the publicly available Merlin (Abecasis et al., *Nat Genet.* 30:97-101 (2002) and Nicolae et al, MERLIN . . . and the Geneticist's Stone?, *Nature Genetics,* 30, 3-4 (2002)), uses the genotype and pedigree information to reconstruct haplotypes and identify likely recombination breakpoints. At step 204, a software tool is then used to facilitate visualization, for example, color-codes data for each chromosome, pattern-codes data for each chromosome, physical shape pop out data for each chromosome, sound-codes data for each chromosome, etc. The visualization software can be illustrated using an exemplary preferred embodiment, "Chromosome Painter" that takes this information on recombination breakpoints and grandparental assignment and color-codes the data for each chromosome so that it can be visualized in color. At step 205, the visual recombination events in the families are provided. The form of the visualization can be of various chart types, for example, line, column, stacked column, floating column, 3D column, Stack 3D column, Parallel 3D column, pie, 3D pie, bar, stacked bar, floating bar, area, stacked area, scatter, polar, mixed, etc. Other forms of visualization can be data in the form of links within the charts or graphs. For example, the links can open up and display detailed data or information regarding the corresponding area. One of ordinary skill in the art would recognize many variations, alternatives, and modifications.

In one aspect genotyping data is obtained using molecular inversion probe technology as described, for example, in U.S. Pat. No. 6,858,412 and in Hardenbol et al., *Genome Res.* 15:269-275 (2005).

In another aspect, genotype data is obtained from high density genotyping arrays such as mapping arrays and resequencing arrays. Mapping arrays are commercially available from Affymetrix, Inc., for example, the Mapping 10K, Mapping 100K and Mapping 500K array sets, and have been described for example, in U.S. Patent Publication Nos. 20040146890, 20060024715, 20050227244 and 20050142577. Methods for using mapping arrays are disclosed, for example, in Kennedy et al., *Nat. Biotech.* 21:1233-1237 (2003), Matsuzaki et al., *Genome Res.* 14:414-425 (2004), Matsuzaki et al., *Nat. Meth.* 1:109-111 (2004) and U.S. Patent Pub. Nos. 20040146890 and 20050042654. Resequencing arrays, are commercially available from Affymetrix, Inc. and have been described, for example, see Cutler, D. J. et. al., *Genome Res.* 11(11), 1913-25, 2001.

Computer implemented methods for determining genotype using data from mapping arrays are disclosed, for example, in Liu, et al., *Bioinformatics* 19:2397-2403 (2003) and Di et al., *Bioinformatics* 21:1958-63 (2005). Computer implemented methods for linkage analysis using mapping array data are disclosed, for example, in Ruschendorf and Numberg, *Bioinformatics* 21:2123-5 (2005) and Leykin et al., *BMC Genet.* 6:7, (2005).

Methods of determining haplotypes are disclosed, for example, in US patent publication 20030170665. For a discussion of haplotype structure see also Lindblad-Toh et al., *Nature* 438:803-19 (2005) and Walsh et al., *Am J. Hum. Genet.* 73:580-90 (2003). For a discussion of methods for inferring haplotype phase from genotype data see, for example, Marchini et al., *Am J Hum Genet* 78:437-450 (2006). All cited references are incorporated herein by reference in their entireties for all purposes.

Figure 2:
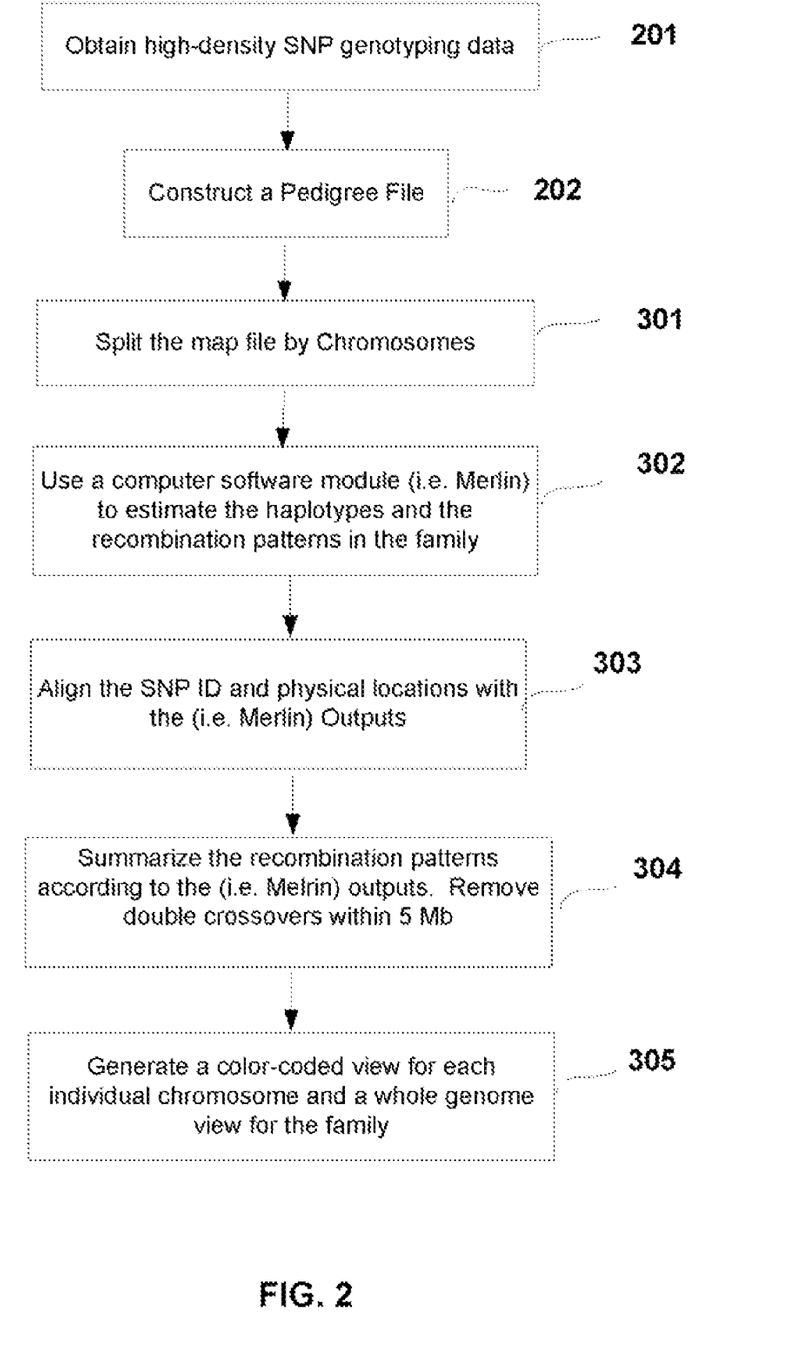
FIG. 2 illustrates a detail level flow of one implementation of the reference method according to an embodiment of the present invention.

In one aspect of the present invention, FIG. 2 illustrates a further detailed view of the instructions for an exemplary preferred process flow of the method used to visualize recombination events in families. This diagram is merely an example, which should not unduly limit the scope of the claims. One of ordinary skill in the art would recognize many variations, alternatives, and modifications. The visualization software can be illustrated using an exemplary embodiment, "Chromosome Painter" that takes this information on recombination breakpoints and grandparental assignment and color-codes the data for each chromosome so that it can be visualized in color. In a preferred embodiment, the Linux (software platform) system is used to generate the files and the Window system is used to generate the input files and the final plots. In another preferred embodiment, the programs: GDAS (GeneChip DNA Analysis Software, available from Affymetrix, Inc.), R scripts, Shell scripts, Perl scripts and Merlin software program are used to visualize recombination events in families.

In a preferred embodiment, the following Step-by step instructions are provided:

1. Obtain high-density SNP genotyping data. This can be obtained by the various technologies mentioned above (i.e. GeneChip® Human Mapping 100 k arrays) as indicated in step 201. Use a compatible DNA software analysis tool (i.e. GDAS) to export the CHP files to the format of the software program that can create a pedigree file (i.e. Merlin formats), including DAT files, PED files and the genetic map files. (specify the file names as zsf_*.dat, zsf_.map, zsf_.ped and separate them by chromosomes).
   A. Create a pedigree file for the samples as indicated in step 202.
   B. Click "Run"-→AttributeImporterTool, browse to input the pedigree file
   C. Specify template "pedigree", and the project name "ZSF"
   D. In DM window, click "tools"→"genotype"→"linkage export".
2. Open the map file, delete those SNPs with genetic map 0.
3. Choose a folder on the chosen software platform (i.e. Linux System) for this project. Ftp the files (dat files, map file and ped files) to your folder on Linux system using text mode. Also ftp the following files under S:/CHUN/ZANDER/program/ to the folder: splitmap.R, hapzsf.sh, alignhap.pl, sorthapout.pl, recomfunc.R sumhaptrunk.R chranno_*.txt. Text mode is recommended in ftp process. Note: chranno_*.txt need to be prepared beforehand according to annotation files on the current genome build (including chromosome, SNPID, physical locations and genetic locations). Splitanno.R is the R script used to split an assembled annotation file (anno35_sorted.map was prepared by manually editing the annotation file from NetAFFX) by chromosomes.
4. Under Linux system, under your folder, type the following, command lines:
   mv zsf_X_01.dat zsf_23.dat
   mv zsf_X_01.ped zsf_23.ped
5. At step 301, the map file is split by chromosomes by typing the command line (note to change the name of the map file, modify the script)
   source/nfs/share/env/R-1.9.0.env (recommend: put in bash_profile before you log on)
   R BATCH splitmap.R tmp.out &
6. At step 302, a computer software module (i.e. Merlin) estimates the haplotypes and the recombination patterns in the family by typing the command line:
   source/nfs/share/env/merlin-0.10.2.env (recommend: put in bash_profile before you log on)
   chmod +x hapzf.sh
   ./hapzsf.sh (note: the names of the dat file, ped file and map file are hard-coded in the script, modify the script when needed. Output file zsfhap_chr*.txt for each chromosome)
7. At step 303, a software tool (i.e. Merlin) is used to align the SNPs with their chromosomal positions and reformat the haplotype outputs by typing the command line:
   perl alignhap.pl (note the name of the map files and the outputs from Merlin are hard-coded, output files zsfhap_*.out for each chromosome)
8. Sort the SNPs by the physical locations:
   perl sorthapout.pl (output files: sortedhap_*.out for each chromosome)
9. At step 304, the recombination patterns are summarized according to the output by running R scripts:
   R BATCH recomfunc.R tmp.out &
   R BATCH sumhaptrunk.R tmp.out &
10. Ftp files (with the names as: lucas_m_chr1.txt, lucas_p_chr1.txt, etc.) to Windows, make sure you have R installed on your machine.
11. physchr.txt is required for this step. This file indicates the start and stop physical locations for each chromosome. Current version fits for Mapping 100K. Open R, change the working directory to the folder with all the transferred files, run script plothap.R. The colored family tree for all the 23 chromosomes will be generated automatically to the current working folder. The file names are: family_chr*.eps for each chromosome (23 in total).
12. At step 305, a summary file for each person in the family dadsum.txt, auntsum.txt, etc.) and a whole genome view for the family are generated by running the script plotgenome.R. The format of the summary file: each row stands for one chromosome; there are 4 columns in total, each column stands for: number of maternal recombinations in this chromosome; the mean length of the haplotype blocks in this chromosome; number of paternal recombination in this chromosome; the mean length of the haplotype blocks in this chromosome.

Figure 4:
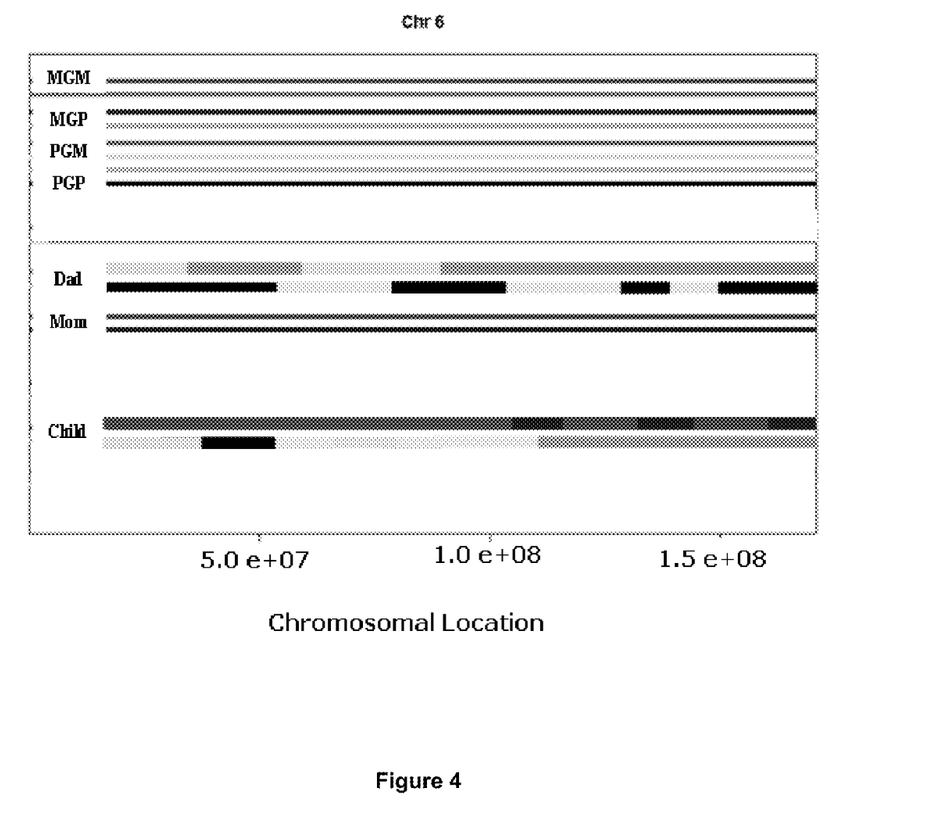
FIG. 4 illustrates an example of a summary chromosome chart (Chromosome 6 according to an embodiment of the present invention.
Figure 5:
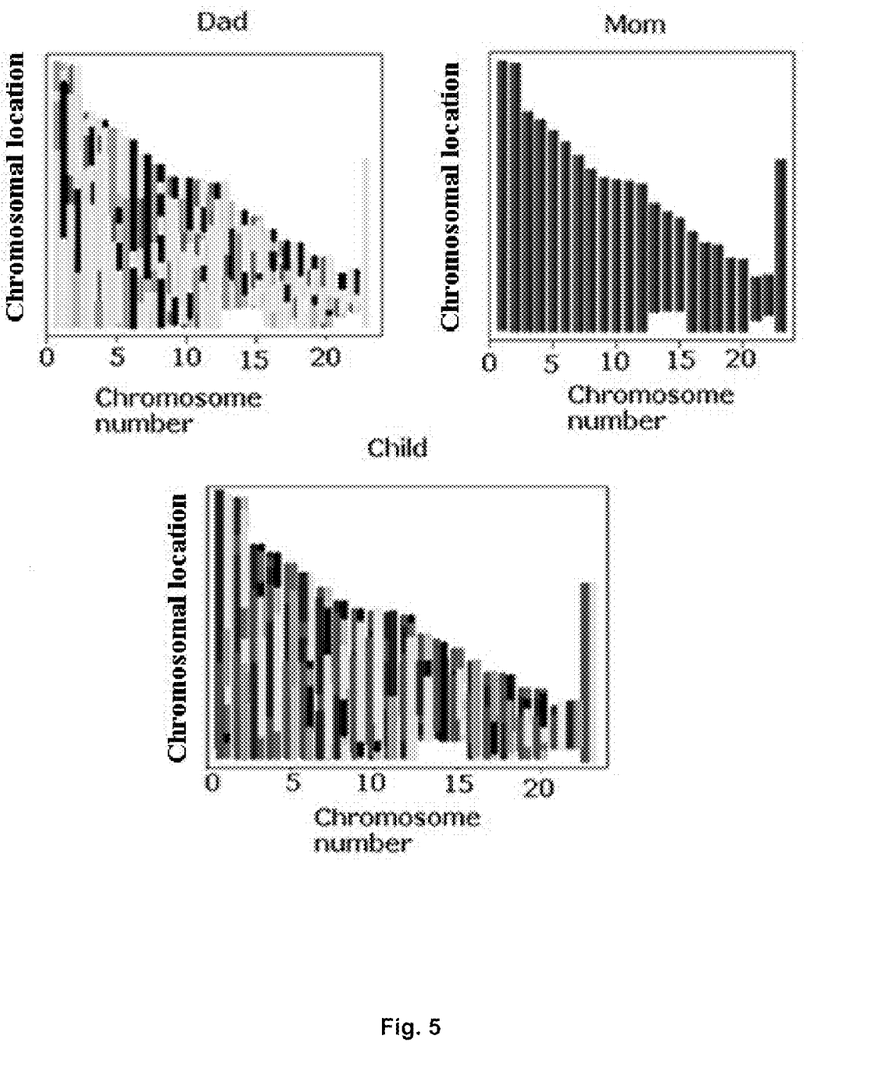
FIG. 5 illustrates an example of a whole genome view according to an embodiment of the present invention.

FIG. 4 illustrates an example of a chromosome summary chart according to a preferred embodiment of the present invention: FIG. 4 shows a chart for Chromosome 6. This diagram is merely an example, which should not unduly limit the scope of the claims. One of ordinary skill in the art would recognize many variations, alternatives, and modifications. FIG. 5 illustrates an example of a whole genome view of a family according to another embodiment of the present invention. This diagram is merely an example, which should not unduly limit the scope of the claims. One of ordinary skill in the art would recognize many variations, alternatives, and modifications.

According to an embodiment of the present invention, a computer program method for visualizing recombination events in a group of individuals is provided which includes a computer code that receives a plurality high density SNP genotyping data and a computer code that generates a pedigree file from the genotyping data. Additionally, the method includes a computer code that receives haplotype and recombination pattern data generated from a computer program that uses the genotyping data and pedigree file to reconstruct the haplotypes and identify the recombination patterns. Moreover, the method includes a computer code that generates the visualization of recombination events in the group of individuals and a computer readable medium that stores the computer codes. In a preferred embodiment, the plurality high density SNP genotyping data are generated from microarrays.

In one aspect of the present invention, the computer program method provides a color-coded view for each individual chromosome. In another preferred embodiment, the computer program method provides a color-coded whole genome view. According to another embodiment of the present invention, the computer program method for visualizing recombination events can be from a family, a village, a country, a population, or any other group of individuals.

According to yet another embodiment of the present invention, a system that visualizes recombination events in a group of individuals is provided which includes a processor, and a computer readable medium coupled to the processor for storing a computer program. The stored computer program includes a computer code that receives a plurality high density SNP genotyping data, a computer code that generates a pedigree file from the genotyping data, a computer code that receives haplotype and recombination pattern data generated from a computer program that uses the genotyping data and pedigree file to reconstruct the haplotypes and identify the recombination patterns, and a computer code that generates the visualization of recombination events in the group of individuals. In a preferred embodiment, the plurality high density SNP genotyping data are generated from microarrays. In another preferred embodiment, the computer program method provides a color-coded view for each individual chromosome. In yet another preferred embodiment, the computer program method provides a color-coded whole genome view. According to another embodiment of the present invention, the computer program method for visualizing recombination events can be from a family, a village, a country, a population, or any other group of individuals.

EXAMPLE

Example 1

DNA samples from individuals in a family are collected and tested with GeneChip® Human Mapping 100K microarrays FIG. 2 outlines the steps that are taken to visualize recombination events in the family. As indicated in step 201, GDAS (GeneChip DNA Analysis Software, available from Affymetrix, Inc.) is used to analyze the high-density SNP genotyping data generated from using the 100K microarrays. GDAS is used to export the CHP files to Merlin-format, including DAT files, PED files and the genetic map files. At step 202, a pedigree file is created. An example of a pedigree file that can be generated is illustrated in FIG. 3. In this family, there are 2 sets of grandparents: PGM (paternal grandmother). POP (paternal grandpa) and MGM (maternal grandmother), MGP (maternal pa). This study also includes the Mom, Dad, and a child.

To prepare for the next step, the map file is opened, and those SNPs with genetic map "0" are deleted. A folder on the Linux System (software platform) for this project is chosen. The files (dat files, map file and ped files) are Ftp'd to the folder on the Linux system by using the text mode. In addition, the following files are placed under S:/CHUN/ZANDER/program/ to the folder: splitmap.R, hapzsf.sh, alignhap.pl, sorthapout.pl recomfunc.R sumhaptrunk.R, chranno_*.txt. The following command lines are typed. "mv zsf_X_01.dat zsf_23.dat" and "mv zsf_X_01.ped zsf_23.ped" under the Linux system, under the operating folder.

At step 301, the file names are specified as zsf_*.dat, zsf_.map, zsf_.ped and the map files are separated by chromosomes by typing the command line "source/nfs/share/env/R-1.9.0.env".

At step 302, the comp ter software module, Merlin is used to estimate the haplotypes and the recombination patterns in the family. The haplotypes and gene flow are estimated by typing the command line: "source/nfs/share/env/merlin-0.10.2.env" and "chmod +x hapzsf.sh./hapzsf.sh".

At step 303, the computer software module, Merlin is used to align the SNP ID and physical locations with the Output from Merlin. The SNPs are aligned with their chromosomal positions and the haplotype outputs are reformatted: "perl alignhap.pl". The SNPs are sorted by their physical locations: "perl sorthapout.pl".

At step 304, the recombination patterns are summarized by manning R scripts: "R BATCH recomfunc.R tmp.out &" and "R BATCH sumhaptrunk.R tmp.out &". Double crossovers within 5 Mb are removed. The files are Ftp'd to Windows and R is verified to be installed on the machine. Physchr.txt, the version which fits for Mapping 100K, is installed. R is opened and the working directory is changed to the folder with all the transferred files, and the script plothap.R is performed.

At step 305, a color-coded view for each individual chromosome summary file for each person in the family and a whole genome view for the family are generated by running script plotgenome.R. Chromosome summary charts for the individual Chromosomes (1-23) are generated for the individuals in the family. FIG. 4, a summary chart for Chromosome 6, is an example of what a summary chromosome chart may look like. The summary chromosome chart provides another way to visualize the data on how each individual is related. In this example, as shown in FIG. 4, the PGM is coded with red and green lines. The POP is coded with dark blue and turquoise lines, MGM is coded with pink and yellow lines, and the MGP is coded with grey and black lines. In this example, the color(s) of the first line indicates related data from the mother side and the color(s) from the second line indicates related data from the father side. In studying this family tree, one can trace the inheritance of a given trait in the family. Factors that are involved in determining patterns of inheritance include the location of the trait-causing gene. These factors can be visually observed in the summary chromosome charts. To obtain a view of all the chromosomes for each person in the family, the whole genome view charts are generated for the family. FIG. 5 is an example of what a whole genome view for a family may look like.

The above description is illustrative and not restrictive. Many variations of the invention will become apparent to those of skill in the art upon review of this disclosure. Merely by way of example, while the invention is illustrated with particular reference to the evaluation of DNA (natural or unnatural), the methods can be used in the analysis from chips with other materials synthesized thereon, such as RNA. The scope of the invention should, therefore, be determined not with reference to the above description, but instead should be determined with reference to the appended claims along with their full scope of equivalents.

What is claimed is:

1. A computer program stored on a non-transitory computer readable medium, the computer program comprising code to perform:
   receiving genotyping data for a group of individuals;
   generating a pedigree file;
   reconstructing one or more haplotypes and identifying one or more recombination events using the genotyping data and the pedigree file; and
   generating a visualization of the one or more recombination events for the group of individuals, wherein the visualization comprises a view of at least one chromosome and a whole genome view for at least two individuals of the group.

2. The computer program of claim 1, wherein the genotyping data is obtained from a microarray.

3. The computer program of claim 1, wherein the genotyping data is obtained from nucleic acid sequencing.

4. The computer program of claim 1, wherein the group of individuals is a family.

5. The computer program of claim 4, wherein the pedigree file comprises information on one or more familial relationships within the group of individuals, and wherein the pedigree file additionally comprises genetic data on the group of individuals.

6. The computer program of claim 1, wherein the pedigree file comprises gender data.

7. The computer program of claim 1, wherein the pedigree file comprises genetic data.

8. The computer program of claim 7, wherein the genetic data comprises disease phenotypes.

9. The computer program of claim 7, wherein the genetic data comprises marker phenotypes.

10. A method of visualizing one or more recombination events for a group of individuals, the method comprising:
  executing computer usable code on a computer, the computer usable code comprising:
    code for receiving genotyping data for a group of individuals;
    code for generating a pedigree file;
    code for reconstructing one or more haplotypes and identifying one or more recombination events using the genotyping data and the pedigree file;
    code for generating a visualization of the one or more recombination events for the group of individuals, wherein the visualization comprises a view of at least one chromosome and a whole genome view for at least two individuals of the group.

11. The method of claim 10, wherein the genotyping data is obtained from a microarray.

12. The method of claim 10, wherein the genotyping data is obtained from nucleic acid sequencing.

13. The method of claim 10, wherein the group of individuals is a family.

14. The method of claim 13, wherein the pedigree file comprises information on one or more familial relationships within the group of individuals, and wherein the pedigree file additionally comprises genetic data on the group of individuals.

15. The method of claim 10, wherein the pedigree file comprises gender data.

16. The method of claim 10, wherein the pedigree file comprises genetic data.

17. The method of claim 16, wherein the genetic data comprises disease phenotypes.

18. The method of claim 16, wherein the genetic data comprises marker phenotypes.

19. A system that visualizes one or more recombination events for a group of individuals, the system comprising:
  a processor; and
  a computer readable storage medium coupled to the processor for storing computer usable code, the computer usable code comprising:
    code for receiving genotyping data for a group of individuals;
    code for generating a pedigree file;
    code for reconstructing one or more haplotypes and identifying one or more recombination events using the genotyping data and the pedigree file; and
    code for generating a visualization of the one or more recombination events for the group of individuals, wherein the visualization comprises a view of at least one chromosome and a whole genome view for at least two individuals of the group.

20. The system of claim 19, wherein the genotyping data is obtained from a microarray.

21. The system of claim 19, wherein the genotyping data is obtained from nucleic acid sequencing.

22. The system of claim 19, wherein the group of individuals is a family.

23. The system of claim 22, wherein the pedigree file comprises information on one or more familial relationships within the group of individuals, and wherein the pedigree file additionally comprises genetic data on the group of individuals.

24. The system of claim 19, wherein the pedigree file comprises gender data.

25. The system of claim 19, wherein the pedigree file comprises genetic data.

26. The system of claim 25, wherein the genetic data comprises disease phenotypes.

27. The system of claim 25, wherein the genetic data comprises marker phenotypes.

28. A computer program stored on a non-transitory computer readable medium, the computer program comprising code to perform:
  receiving genotyping data for a group of individuals, wherein the group of individuals is a family;
  generating a pedigree file, wherein the pedigree file comprises information on one or more familial relationships within the group of individuals, and wherein the pedigree file additionally comprises genetic data on the group of individuals;
  reconstructing one or more haplotypes and identifying one or more recombination events using the genotyping data and the pedigree file, wherein double crossovers within a minimum double crossover distance are removed from the one or more recombination events; and
  generating a visualization of the one or more recombination events for the group of individuals.

29. The computer program of claim 28, wherein the genotyping data is obtained from a microarray.

30. The computer program of claim 28, wherein the genotyping data is obtained from nucleic acid sequencing.

31. The computer program of claim 28, wherein the genetic data comprises disease phenotypes.

32. The computer program of claim 28, wherein the genetic data comprises marker phenotypes.

33. The computer program of claim 28, wherein the visualization comprises a view of at least one chromosome for at least two individuals of the group.

34. The computer program of claim 28, wherein the visualization comprises a whole genome view for at least two individuals of the group.

35. The computer program of claim 28, wherein the minimum double crossover distance is 5 Mb.

36. A method of visualizing one or more recombination events for a group of individuals, the method comprising:
  executing computer usable code on a computer, the computer usable code comprising:
    code for receiving genotyping data for a group of individuals;
    code for generating a pedigree file, wherein the pedigree file comprises information on one or more familial relationships within the group of individuals, and wherein the pedigree file additionally comprises genetic data on the group of individuals;
    code for reconstructing one or more haplotypes and identifying one or more recombination events using the genotyping data and the pedigree file, wherein double crossovers within a minimum double crossover distance are removed from the one or more recombination events; and code for generating a visualization of the one or more recombination events for the group of individuals.

37. The method of claim 36, wherein the genotyping data is obtained from a microarray.

38. The method of claim 36, wherein the genotyping data is obtained from nucleic acid sequencing.

39. The method of claim 36, wherein the genetic data comprises disease phenotypes.

40. The method of claim 36, wherein the genetic data comprises marker phenotypes.

41. The method of claim 36, wherein the visualization comprises a view of at least one chromosome for at least two individuals of the group.

42. The method of claim 36, wherein the visualization comprises a whole genome view for at least two individuals of the group.

43. The method of claim 36, wherein the minimum double crossover distance is 5 Mb.

44. A system that visualizes one or more recombination events for a group of individuals, the system comprising:
   a processor; and
   a computer readable storage medium coupled to the processor for storing computer usable code, the computer usable code comprising:
      code for receiving genotyping data for a group of individuals, wherein the group of individuals is a family;
      code for generating a pedigree file, wherein the pedigree file comprises information on one or more familial relationships within the group of individuals, and wherein the pedigree file additionally comprises genetic data on the group of individuals;
      code for reconstructing one or more haplotypes and identifying one or more recombination events using the genotyping data and the pedigree file, wherein double crossovers within a minimum double crossover distance are removed from the one or more recombination events; and
      code for generating a visualization of the one or more recombination events for the group of individuals.

45. The system of claim 44, wherein the genotyping data is obtained from a microarray.

46. The system of claim 44, wherein the genotyping data is obtained from nucleic acid sequencing.

47. The system of claim 44, wherein the genetic data comprises disease phenotypes.

48. The system of claim 44, wherein the genetic data comprises marker phenotypes.

49. The system of claim 44, wherein the visualization comprises a view of at least one chromosome for at least two individuals of the group.

50. The system of claim 44, wherein the visualization comprises a whole genome view for at least two individuals of the group.

51. The system of claim 44, wherein the minimum double crossover distance is 5 Mb.

* * * * *